US010688469B2

(12) United States Patent
Selhuber-Unkel et al.

(10) Patent No.: US 10,688,469 B2
(45) Date of Patent: Jun. 23, 2020

(54) MICROPOROUS HYDROGELS

(71) Applicant: Christian-Albrechts-Universität zu Kiel, Kiel (DE)

(72) Inventors: Christine Selhuber-Unkel, Kiel (DE); Iris Hölken, Schönkirchen (DE); Sören Björn Gutekunst, Limburgerhof (DE); Rainer Adelung, Kiel (DE)

(73) Assignee: Christian-Albrechts-Universität zu Kiel, Kiel (DE)

( * ) Notice: Subject to any disclaimer, the term of this patent is extended or adjusted under 35 U.S.C. 154(b) by 295 days.

(21) Appl. No.: 15/571,892

(22) PCT Filed: May 6, 2016

(86) PCT No.: PCT/EP2016/060160
§ 371 (c)(1),
(2) Date: Nov. 6, 2017

(87) PCT Pub. No.: WO2016/177872
PCT Pub. Date: Nov. 10, 2016

(65) Prior Publication Data
US 2018/0161759 A1    Jun. 14, 2018

(30) Foreign Application Priority Data
May 7, 2015  (EP) .................................... 15166793

(51) Int. Cl.
*B01J 20/28* (2006.01)
*A61L 12/14* (2006.01)
(Continued)

(52) U.S. Cl.
CPC ........ *B01J 20/28095* (2013.01); *A01N 25/34* (2013.01); *A61L 12/14* (2013.01);
(Continued)

(58) Field of Classification Search
CPC ............ B01J 20/28095; B01J 20/28047; B01J 20/28085; B01J 20/261; B01J 20/3057;
(Continued)

(56) References Cited

U.S. PATENT DOCUMENTS 6,673,285 B2    1/2004  Ma
9,770,535 B2    9/2017  Mooney et al.
(Continued)

FOREIGN PATENT DOCUMENTS

DE    102010012385 A1    9/2011
WO     2014063128 A1    4/2014

OTHER PUBLICATIONS

Patel et al., Contact lens-related microbial keratitis: recent outbreaks, Wolters Kluwer Health, p. 302-306, 2008.
(Continued)

*Primary Examiner* — David C Mellon
(74) *Attorney, Agent, or Firm* — Thomas|Horstemeyer, LLP

(57) ABSTRACT

The invention relates to a porous hydrogel matrix having substantially interconnected tunnel-shaped micropores with a three-dimensional configuration of an interconnected hollow tetrapod network. Such matrices may be used to entrap motile cells that migrate into the micropores of said matrix. The matrices of the invention are formed by a method comprising the steps of providing a solution of a hydrogel-forming material, providing a template material with a three-dimensional configuration corresponding to the negative configuration of the desired interconnected porous structure of the hydrogel material, said template material comprising interconnected zinc oxide tetrapod (t-ZnO) networks, casting the solution of hydrogel-forming material
(Continued)

onto the template and removing the template material from the hydrogel material by acid hydrolysis of the template material.

15 Claims, 4 Drawing Sheets

(51) Int. Cl.
    *C08J 9/26*     (2006.01)
    *B01J 20/30*     (2006.01)
    *A01N 25/34*     (2006.01)
    *B01J 20/26*     (2006.01)
    *B29C 67/20*     (2006.01)
    *C02F 1/28*     (2006.01)
    *C08J 9/00*     (2006.01)
    *B29K 33/00*     (2006.01)
    *B29K 105/00*     (2006.01)

(52) U.S. Cl.
    CPC ....... *B01J 20/261* (2013.01); *B01J 20/28047* (2013.01); *B01J 20/28085* (2013.01); *B01J 20/3057* (2013.01); *B29C 67/202* (2013.01); *C02F 1/285* (2013.01); *C08J 9/0038* (2013.01); *C08J 9/26* (2013.01); *B29K 2033/26* (2013.01); *B29K 2105/0061* (2013.01); *B29K 2909/02* (2013.01); *C02F 2303/04* (2013.01); *C08J 2201/026* (2013.01); *C08J 2201/0442* (2013.01); *C08J 2205/022* (2013.01); *C08J 2205/044* (2013.01); *C08J 2205/05* (2013.01); *C08J 2205/052* (2013.01); *C08J 2207/10* (2013.01); *C08J 2207/12* (2013.01); *C08J 2333/02* (2013.01); *C08J 2333/10* (2013.01); *C08J 2333/26* (2013.01); *C08J 2371/02* (2013.01)

(58) Field of Classification Search
    CPC .... B01J 20/268; B01J 20/305; B01J 20/3064; B01J 20/3071; B01J 20/3085; B29C 67/202; A01N 25/34; A61L 12/14; C08J 2201/026; C08J 2333/02; C08J 2207/12; C08J 2371/02; C08J 2333/10; C08J 2205/052; C08J 2333/26; C08J 2207/10; C08J 2205/05; C08J 2205/044; C08J 2205/022; C08J 2201/0442; C08J 9/0038; C08J 9/26; C02F 2303/04; C02F 1/285; B29K 2909/02; B29K 2105/0061; B29K 2033/26

See application file for complete search history.

(56) References Cited

U.S. PATENT DOCUMENTS

| | | | |
|---|---|---|---|
| 2006/0088470 | A1 | 4/2006 | Anders et al. |
| 2009/0087641 | A1* | 4/2009 | Favis ............... A61L 27/18 428/304.4 |
| 2016/0200891 | A1* | 7/2016 | Virgilio ............ C08J 9/26 424/492 |
| 2016/0339145 | A1* | 11/2016 | Hegmann ........... A61L 27/18 |
| 2018/0369785 | A1* | 12/2018 | Fee ................. B01J 20/3071 |

OTHER PUBLICATIONS

Walochnik et al., Die Behandlung der Acanthamoeba-Keratitis: Möglichkeiten, Probleme und neue Wege, Wien Klin Wochenschr 115[Suppl 3]: p. 10-17, 2003.
Johnston et al., Resistance of Acanthamoeba Cysts to Disinfection in Multiple Contact Lens Solutions, Journal of Clinical Microbiology, p. 2040-2045, 2009.
Gutekunst et al., Influence of the PDMS substrate stiffness on the adhesion of Acanthamoeba castellanii, Beilstein J. Nanotechnol. 5, p. 1393-1938, 2014.
Mlishra et al., Fabrication of Macroscopically Flexible and Highly Porous 3D Semiconductor Networks from Interpenetrating Nanostructures by a Simple Flame Transport Approach, Part. Part. Syst. Charact. 30, p. 775-783, 2013.
Mishra et al., Versatile Fabrication of Complex Shaped Metal Oxide Nano-Microstructures and Their Interconnected Networks for Multifunctional Applications, KONA Powder and Particle Journal No. 31, p. 92-110, 2014.
Mecklenburg et al., Aerographite: Ultra Lightweight, Flexible Nanowall, Carbon Microtube Material with Outstanding Mechanical Performance, Adv. Mater., p. 1-5, 2012.
International Search Report issued by the European Patent Office for PCT/EP2016/060160, dated Nov. 8, 2016.

* cited by examiner

MICROPOROUS HYDROGELS

FIELD OF THE INVENTION

The present invention relates to porous hydrogels with interconnected pores, to a method for making such hydrogels and to the use of such hydrogels to entrap motile cells, as well as a kit useful for cleaning contact lenses.

BACKGROUND OF THE INVENTION

Three-dimensional (3D) scaffolds are the choice materials for mimicking the natural environment of many cell types, which in vivo are normally integrated into well-structured and dense structures. Thus, 3D materials for cell culture and for studies on cell adhesion and cell migration have become highly relevant in many applications.

The architectural features in terms of pore morphology (pore size, shape, pore surface characteristics, porosity and interconnectivity) are manifestly important for the performance of such 3D environments. A wide range of techniques have been proposed to design 3D matrices, e.g. selective laser sintering, multiphoton lithography/direct laser writing, stereolithography, bioplotting or 3D printing/fused deposition modeling. In general these techniques are quite complex, expensive and do not offer great flexibility in terms of materials to be used and/or of obtainable structures.

A further common technique to generate 3D environments consists of reverse fabrication or pore-leaching, where pores are introduced into a bulk material by dissolving salt crystals or other dissolvable particles that were previously embedded in that bulk material. Such techniques have the disadvantage that the pores are mainly inverse-opal shaped, so that the interconnectivity of the pores is dependent on the pore size and density, i.e. a high degree of interconnectivity implies large pore sizes. For many applications, however, it is advantageous to maximize the contact between the cells and the scaffold by using pores that are approximately equal to the cell size. Through this, a large contact area of cell and the pore surface is ensured. Under such circumstances, the impact of material parameters such as stiffness or functionalization is much higher than in materials with large pores. U.S. Pat. No. 6,673,285 teaches the reverse fabrication of porous materials with a pre-designed three-dimensional negative replica of the desired pore configuration. The methods disclosed therein are reported to generate materials with high porosity and interconnected large pores, generally larger than cell size. However, this patent does not teach specifically how pore interconnectivity may be achieved independently from pore density and how to define shape and size of the matrix, its porosity as well as its stiffness independently from each other.

There is an ongoing need for 3D structured materials that mimic complex 3D structures found in vivo as well as for efficient, easy and inexpensive methods for fabricating such 3D materials. In particular there is a need for methods to generate scaffolds with flexible, easily customizable porosity characteristics and with pores that are approximately equal to the cell size.

The use of porous scaffolds as cell traps has been proposed as a means to eliminate undesirable cells in vivo. For example, a method to recruit and eliminate metastatic cancer cells, wherein cancer cells migrate and accumulate in a porous matrix is described in WO 2014063128. Another example is the device comprising a porous scaffold composition which attracts, adheres, captures and eliminates targeted undesirable cells as disclosed in U.S. patent application Ser. No. 12/665,761. In both cases, bioactive agents in the scaffold compositions are used to attract and/or destroy the undesirable cells.

Acanthamoeba castellanii (A. castellanii) are free-living protists often found in tap water and swimming pools. If transmitted to the eye they can cause acanthamoeba keratitis, which has become a serious disease among contact lens users. An estimated 85% of acanthamoeba keratitis cases are related to contact lens usage (Patel et al. Current Opinion in Ophthalmology 2008, 19, 302-306). Until 2003, more than 2000 cases of this extremely painful partial destruction of the cornea have been reported (Walochnik et al. Wien Klin Wochenschr. 2003, 115, 10), and even further cases occurred during the 2004 to 2007 outbreak of acanthamoeba keratitis in multiple states of the US (Johnston et al. Journal of Clinical Microbiology 2009, 47, 2040-2045). Infections of contact lens users with A. castellanii are mainly due to wrong contact lens care, but have also been associated with the resistance of A. castellanii cysts to contact lens cleaning solutions.

Using a combined treatment of a special multipurpose solution and peroxide treatment minimizes the risk for A. castellanii growth even on lens materials with high water content, yet not all hydrogen peroxide solutions on the market kill A. castellanii. Although some studies also suggest that silver nanoparticles are a promising strategy to kill A. castellanii and thus prevent infection, recent studies have shown that even for small silver concentrations, cytotoxicity against mammalian cells is present. Thus, it is questionable if silver-coated contact lens storage cases are the right strategy to prevent A. castellanii infections, as this would mean a constant exposure of the eye's epithelial cells to silver ions.

Contact lenses with high water content are currently highly appreciated among contact lens users, but unfortunately A. castellanii adhesion increases with increasing water content of the lens. A way to prevent A. castellanii infections might be to adapt the mechanical properties of the contact lens material. Recent studies have shown that substrate stiffness strongly controls the adhesion and differentiation of mammalian cell types. However, it was shown that this strategy is not suitable for contact lenses, as the mechanical stiffness threshold for A. castellanii adhesion is far below any stiffness value suitable for contact lens materials (Gutekunst et al. Beilstein Journal of Nanotechnology 2014, 5, 1393-1398).

Accordingly, there exists an ongoing need to develop new methods for minimizing the presence of A. castellanii in contact lens environments, thus helping to prevent A. castellanii infections in contact lens users. Sequestering the cells from the contact lens solution, especially in a non-toxic way, e.g. without the use of bioactive agents such as chemoattractants, would be an ideal way to minimize cell proliferation and reduce A. castellanii infections.

OBJECT OF THE INVENTION

In view of the above, it is an object of the present invention to provide a porous hydrogel matrix with substantially interconnected tunnel-shaped micropores, where the interconnectivity is mostly independent of the pore density and where shape and size of the matrix, its porosity as well as its stiffness can be defined largely independently from each other. It is a further object of the invention to provide an efficient, easy and inexpensive method for forming a porous matrix with substantially interconnected tunnel-shaped micropores with flexible, easily customizable porosity characteristics and with pores that are approximately equal to the cell size. Such a matrix may be used to entrap motile cells in general, and especially to sequester and remove *A. castellanii* from contact lens environments.

SUMMARY OF THE INVENTION

The above object is solved by a method for forming a porous hydrogel matrix having substantially interconnected tunnel-shaped micropores, said method comprising the steps of providing a solution of a hydrogel-forming material, providing a template material with a three-dimensional configuration corresponding to the negative configuration of the desired interconnected porous structure of the hydrogel material, said template material comprising, preferably, consisting of interconnected zinc oxide constituent networks, preferably, interconnected zinc oxide tetrapod (t-ZnO) networks, casting the solution of hydrogel-forming material onto the template and removing the template material from the hydrogel material by acid hydrolysis of the template material.

The method according to the invention enables the formation of porous hydrogel matrices having substantially interconnected tunnel-shaped micropores with a three-dimensional configuration of an interconnected hollow tetrapod network. Such matrices may be used to entrap motile cells that migrate into the micropores of said matrix.

These figures are intended to be merely illustrative and non-limiting.

DETAILED DESCRIPTION OF THE INVENTION

The method of the invention comprises the steps of:
a) providing a solution of a hydrogel-forming material;
b) providing a template material with a three-dimensional configuration corresponding to the negative configuration of the desired interconnected porous structure of the hydrogel material, said template material comprising, preferably, consisting of interconnected zinc oxide constituent networks, preferably interconnected zinc oxide tetrapod networks;
c) casting the solution of hydrogel-forming material onto the template;
d) removing the template material from the hydrogel material by acid hydrolysis of the template material,
to yield a porous hydrogel matrix having substantially interconnected tunnel-shaped micropores.

Of course, steps a and b can be performed in any order.

Figure 1:
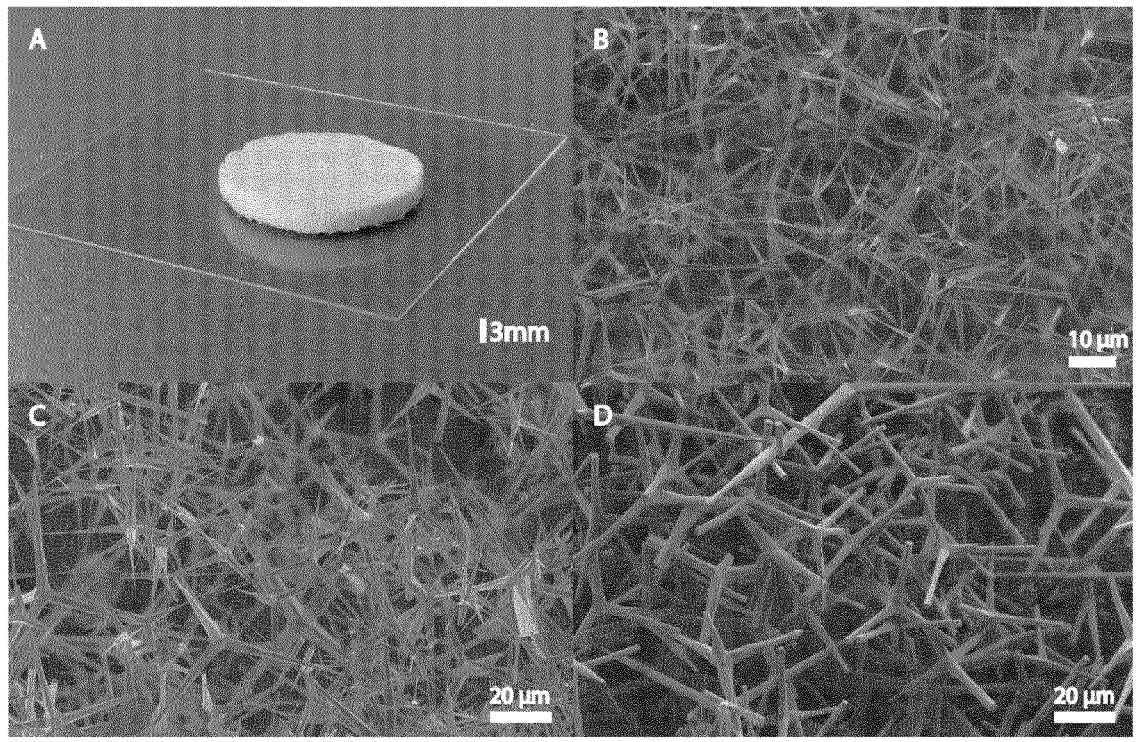
FIG. 1 shows interconnected networks of ZnO tetrapods (A) Macroscopic view of a t-ZnO tablet (3 mm×11 mm); (B-D) SEM images of t-ZnO networks.

To generate the porous structures as described herein, interconnected zinc oxide tetrapod (t-ZnO) networks are preferably used as sacrificial template material. It is to be understood that a tetrapod or a tetrapod unit in the context of the present invention means an essentially regular, tetrahedron-based geometric form wherein four arms stretch from a junction in the center to the corners of a tetrahedron shape. The angle between the arms of such a regular tetrapod, the so called tetrahedron angle, is approximately 109.5°.

t-ZnO may be synthesized by flame transport synthesis according to Adelung et al. (DE102010012385), Mishra et al. (Part Part Syst Char 2013, 30, 775-783; Kona 2014, 30, 92-110) and Mecklenburg et al. (Adv. Mater 2012, 24, 3486-3490) or by any other means known to those skilled in the art. ZnO networks used according to the invention are generally sintered from single ZnO microparticles. The t-ZnO fabrication and further reheating (1100° C.-1200° C., 4-6 h, preferably, about 5 h) procedure guarantees the generation of structures with self-organized interconnectivity. The synthesis method has the further advantage that the ZnO network can be formed with different morphologies and sizes of its single constituents. In a preferred embodiment, the single constituents of the network are tetrapod-shaped units (FIG. 1, B-D). However, other forms of the ZnO single constituents such as multipod, sea urchin or platelets are also possible, or the network may contain mixtures of different forms. Preferably, the ZnO network comprises at least 50%, preferably, at least 60%, at least 70%, at least 80%, at least 90%, at least 95% or at least 99% or 100% interconnected zinc oxide tetrapods (% m t-ZnO/m template). The template may also comprise other components than ZnO, provided they can also be removed by the acid hydrolysis step or an additional step compatible with the matrix of the invention and its use. Preferably, the template consists of ZnO or at least comprises at least 90%, preferably 99% ZnO (m/m).

Generally, the size of the tetrapod-shaped units in the t-ZnO template to be used according to the invention can be chosen depending on synthesis conditions (such as size of initiator particles and temperature). The diameter of the single tetrapod units of the network may vary between 40 µm and 400 µm. Accordingly, tetrapod arm lengths may vary between 20 µm and 200 µm. Tetrapod arm diameters between 500 nm and 15 µm are possible. In general, the tetrapod-shaped units in the t-ZnO template to be used according to the invention have an aspect ratio, i.e. the ratio arm length/arm diameter, greater than 10.

In general, the density of the ZnO networks to be used according to the invention can also be chosen depending on synthesis conditions. The filling factor of the t-ZnO template may vary from 4 to 53 vol.-%. Commonly used filling factors are in the range from 4-27 vol.-%. Most importantly, the tetrapod units in the networks are interconnected even with filling factors down to 4 vol.-%, since interconnectivity is an inherent result of the fabrication procedure of t-ZnO.

The ZnO template, preferably, t-ZnO template to be used according to the invention may be present in a macroscopic form of any shape, as for example tablets (FIG. 1 A), discs, mugs, etc.

An important feature of ZnO in connection with the invention is that its hydrophilicity may be varied. The polarity and hydrophilicity of t-ZnO are important to enable the wetting of the template with a hydrogel-forming material, making a template-guided hydrogel polymerization possible in the first place. The hydrophilicity of the t-ZnO may be adjusted by pH variation or UV irradiation or by any other means known to those skilled in the art.

According to the invention, the hydrogel-forming material to be cast onto the t-ZnO template is compatible with wetting of the template. Moreover, upon polymerization, the hydrogel-forming material must be resistant to the treatment used to remove the template. Such a hydrogel-forming material may be a biocompatible material, for example preferably polyacrylamide, but also polyethylene glycol (PEG), poly(N-isopropylacrylamide) (PNIPAAm), poly(2-hydroxyethyl methacrylate) (PHEMA), poly(acrylic acid) (PAA) and/or possible copolymers. Further examples of hydrogel-forming materials are known to those skilled in the art. Methods to control the physical parameters of a hydrogel, e.g. controlling the stiffness by varying cross-linker density, are known in the art.

The hydrogel-forming material is provided and cast onto the ZnO template, preferably, t-ZnO template. After cross-linking of the hydrogel, the ZnO is removed by dissolving it with an acid treatment. Such a treatment may be performed for example with HCl or other acid solutions, and at pH values in the range of 1.5 to 4. Hydrolysis is performed until the template is dissolved, e.g., for about 1-120 h, such as 12-24 hours. As an example, the removal procedure of the t-ZnO from a polyacrylamide matrix according to the invention is illustrated at the macroscopical scale in FIG. 2 and at the microscopical scale in FIG. 3.

After ZnO hydrolysis, the hydrogel matrix may be washed to remove the acid, e.g., in water, aqueous buffer, cell-culture medium or a solution comprising a chemotaxis-inducing substance. The matrix may be equilibrated to physiological conditions for the desired cell application. During hydrolysis, washing and equilibration or storage in aqueous solution, the matrix swells.

For sterilization, the polymer matrix may be repeatedly dipped into 70% ethanol for 1-5 min and subsequently repeatedly washed with sterile cell medium. Polymers with a glass transition temperature (Tg) above 120° C. may also be disinfected by autoclaving in solution. Polyacrylamide is a preferred matrix material according to the invention, as it is not destroyed by ZnO hydrolysis in mild acid treatment. In addition, polyacrylamide as choice hydrogel enables the delivery of nutrients and gas exchange for the cells inside the matrix. Moreover, its swelling properties provide the possibility to incorporate functional agents such as chemotactic agents or drugs into the hydrogel.

Through the method of the present inventions, a porous hydrogel matrix having interconnected tunnel-shaped micropores is formed, in which the tunnel-shaped micropores have a three-dimensional configuration corresponding to the negative configuration of the sacrificial template material, specifically corresponding to an interconnected hollow tetrapod network. The present invention thus provides a porous hydrogel matrix with interconnected tunnel-shaped micropores wherein a majority (i.e., more than 50%, preferably, 60-90% or 70-80%) of micropores forms a tetrahedron angle (ca. 109.5°) at the micropore junctions. For this assessment, each tetrapod arm is considered a micropore.

Figure 4:
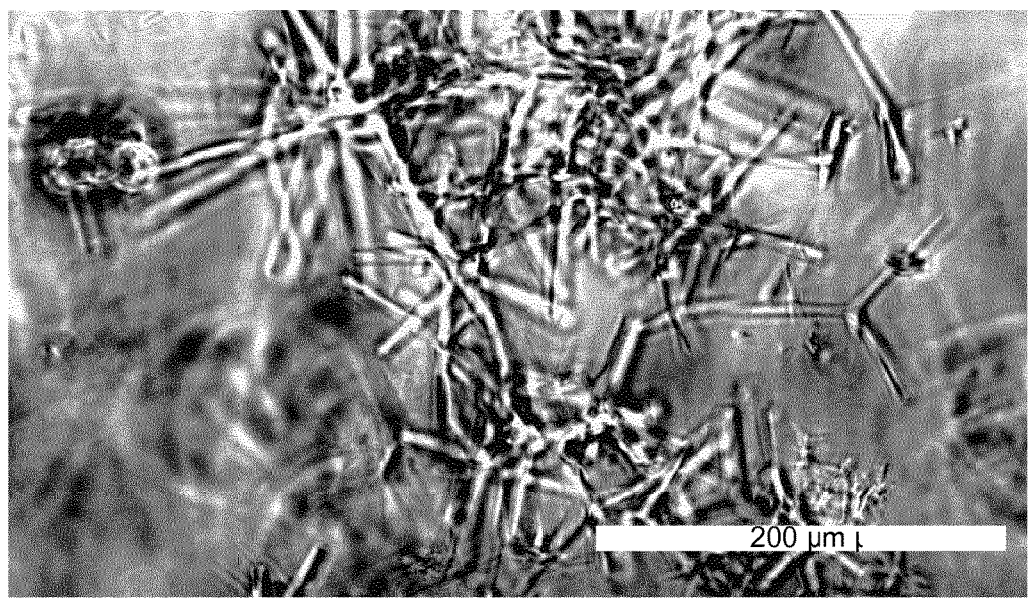
FIG. 4 is a phase contrast image of a microporous polyacrylamide matrix according to the invention.
Figure 5:
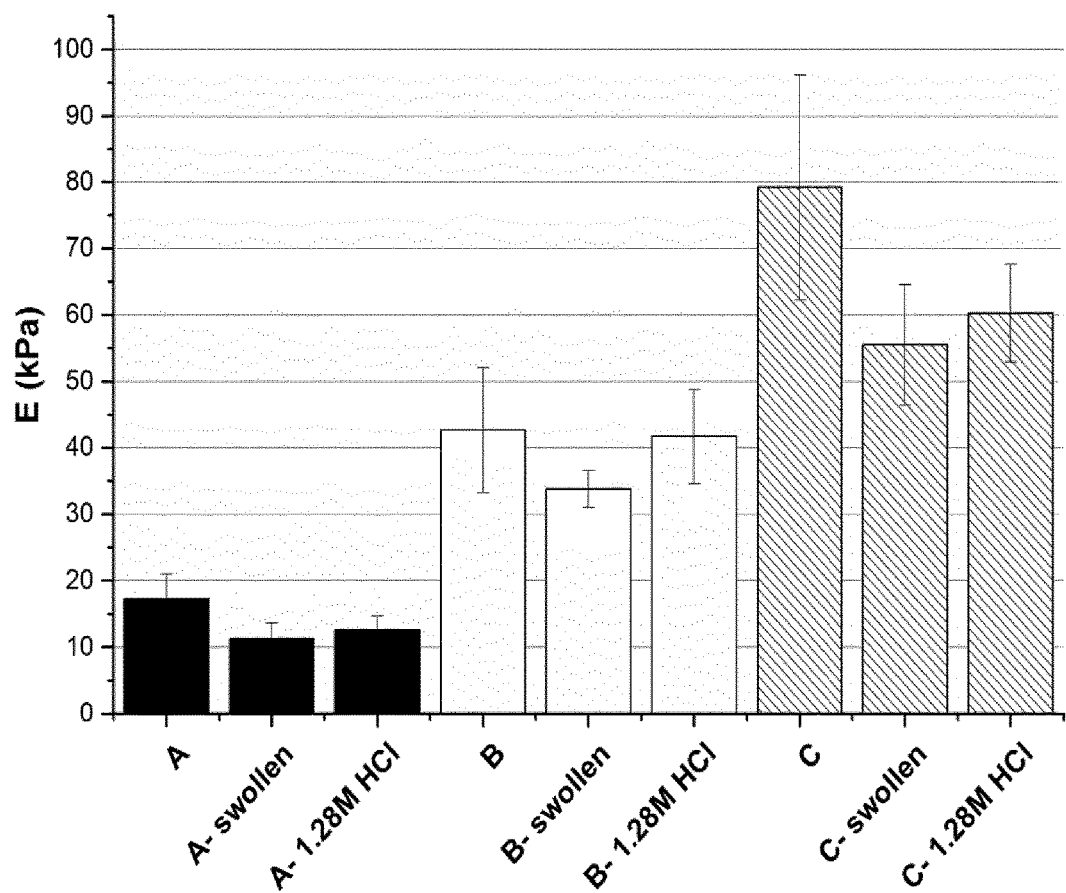
FIG. 5 is a graph representing Young's modulus of polyacrylamide for different mixtures according to Table 1 (A, B and C, Example 5) directly after synthesis, after 2 days of swelling in water and swollen samples after 24 h in 1.28 M HCl. The measurements were carried out in three independent repeats, each at least in triplicate. Error bars denote standard deviation.

FIG. 4 shows an example of a microporous hydrogel matrix according to the invention. The self-organized, not pre-designed interconnectivity of the matrices according to the invention is largely independent of the pore density. Moreover, micropore morphology, shape and size of the matrix, its porosity as well as its stiffness can be defined largely independently from each other by varying the characteristics of the hydrogel-forming material and of the template sacrificial t-ZnO.

Tunnel architecture parameters in porous hydrogel matrices according to the invention before swelling will vary in parallel to the characteristics of the template sacrificial t-ZnO used. Thus, the diameter of the single hollow tetrapod units of the network may vary between 40 μm and 400 μm. Accordingly, tunnel-shaped micropore lengths may vary between 20 μm and 200 μm. Tunnel-shaped micropore diameters between 500 nm and 15 μm are possible.

Furthermore, the tunnel-shaped pores preferably display a ratio tunnel length/tunnel diameter greater than 10.

Moreover, the pore density of the porous unswollen hydrogel matrices according to the invention may vary from 4 to 53 vol.-%, and preferably from 4 to 27 vol.-%. In general, pore interconnectivity in microporous materials known is the art is dependent on the volumetric share of the pores, a high degree of interconnectivity is only achieved in materials with high pore densities. A special distinguishing feature of the porous hydrogel matrices according to the invention is that the tunnel-shaped pores are essentially completely interconnected, and that this interconnection is mostly independent of pore density, i.e. interconnectivity is present even at very low pore densities. In this way, there are substantially no unusable hollow spaces inside the matrix completely enclosed by hydrogel material and thus isolated from the rest of the pores, preferably, less than 20%, less than 10%, less than 5% or less than 1% (v/v) of micropores are isolated from the rest of the pores.

Due to the underlying tetrapod geometry, the tunnel-shaped pores may be further characterized in that the pores are elongate, tunnel-shaped, and not inverse opal shaped as often in the art. In a porous hydrogel matrix of the invention having interconnected tunnel-shaped micropores, in the majority of cases, tunnel intersections join four tunnels, of which, on average, two form dead-ends. These dead-ends may serve as areas for stable cell growth and/or to delay the movement of motile cells, thus contributing to the cell sequestering effect. More than four intersections or more or less than two dead-ends, e.g., four dead-ends, three dead-ends, one dead-end or no dead-end, are also possible, however less common.

Porous hydrogel matrices according to the invention render it possible to maximize the contact between cells and the inner surface of the pores of the hydrogel, as the pores may have dimensions corresponding approximately to cell size. Hence, the impact of material parameters such as stiffness and functionalization will be much higher than in materials with very large pores. The stiffness of the hydrogel may be controlled by varying the nature of the polymer, its cross-linker density and the swelling parameters.

Porous hydrogel matrices according to the invention may be easily and inexpensively fabricated, since the method of the present invention may be performed continuously or in batches, both manually and/or automatically. The matrices according to the invention are obtainable by the method of the invention described herein.

Figure 6:
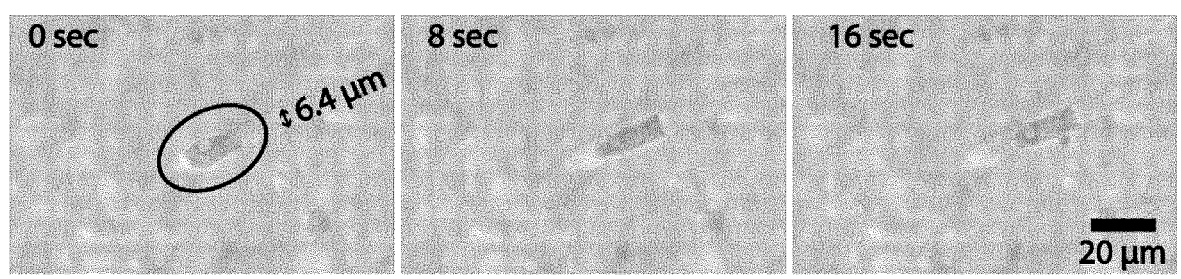
FIG. 6 shows phase contrast images of *A. castellanii* moving inside a microporous polyacrylamide matrix. The circle indicates an *Acanthamoeba* moving inside a tunnel-shaped pore marked by the arrow.
Figure 7:
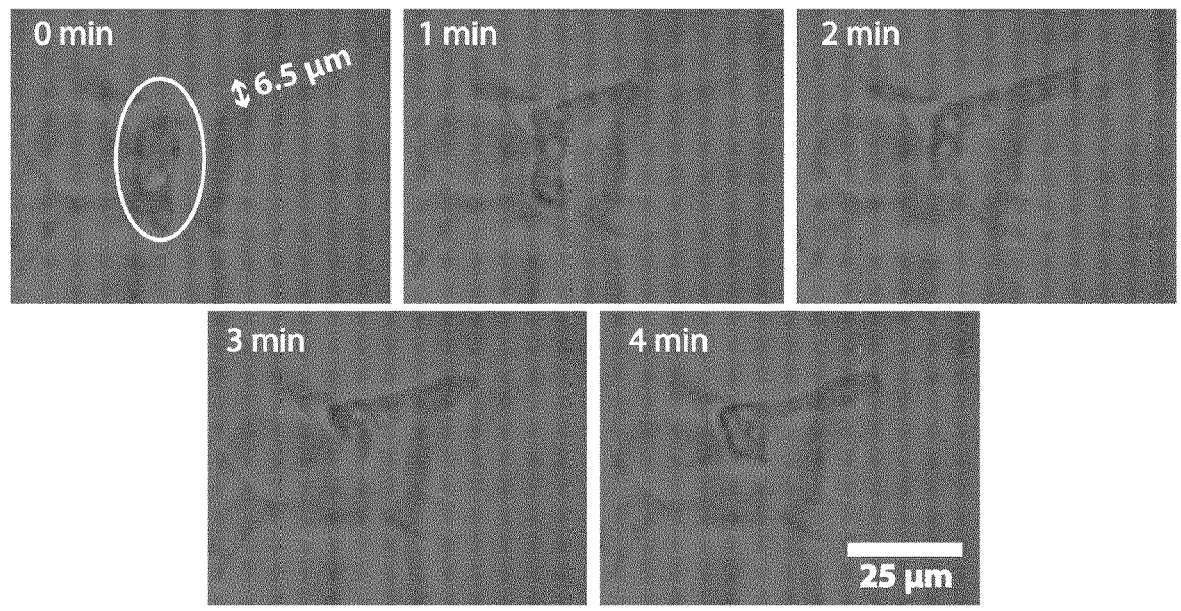
FIG. 7 shows phase contrast images of *A. castellanii* moving inside a microporous polyacrylamide matrix containing a chemotaxis inducing substance (cAMP). The circle indicates an *Acanthamoeba* moving into a tunnel-shaped pore marked by the arrow.

The presence of small tetrapod agglomerates and multipodes of the t-ZnO template can lead to larger cavities in the hydrogel. These may act as a restraining room for motile cells, e.g. for amoebae, e.g., Acanthamoebae, such as *A. castellanii*. After migrating through the tunnel-shaped pores corresponding to tetrapod arms, as illustrated in FIGS. 6 and 7, *A. castellanii* tend to stay in such larger cavities in groups and rest there for several hours if kept under constant environmental conditions. In this way, the material may be used as a cell trap. Cavity-like structures large enough to enclose more than one amoeba are especially suited to entrap the cells. In addition, the maze-like structure of the tunnels hinders the amoebae from leaving the substrate again once they have entered the structure. The matrix of the invention may thus further comprise larger cavities in the hydrogel capable of enclosing more than one amoeba.

Accordingly, it is an object of the present invention to provide the use of a matrix as described herein to entrap motile cells, which may migrate into the micropores of the matrix. The invention also provides a method of reducing or eliminating motile cells, e.g., *A. castellanii*, from a solution or from an object in contact with a solution (e.g., a contact lens in contact with a contact lens cleaning or storage solution), comprising contacting said solution with a matrix of the invention. The solution may be water (e.g., drinking water, tap water or swimming pool water), contact lens cleaning and/or storage solution, or cell culture medium, preferably contact lens storage solution. The contacting may be for about 2 minutes to about a week, preferably, about 5 minutes to overnight, or about 15 minutes to 2 hours, about 30 minutes to 1 hour. The temperature is only limited by conditions wherein the cells are motile. Preferably, the contacting is performed at room temperature (e.g., about 20-25° C.), but it may also be performed at higher temperatures, e.g., about 37° C.

In another embodiment, the matrix of the invention may also be used for cultivating motile cells in contact with said matrix. Said motile cells may migrate into the micropores of said matrix and propagate there under suitable conditions.

Figure 8:
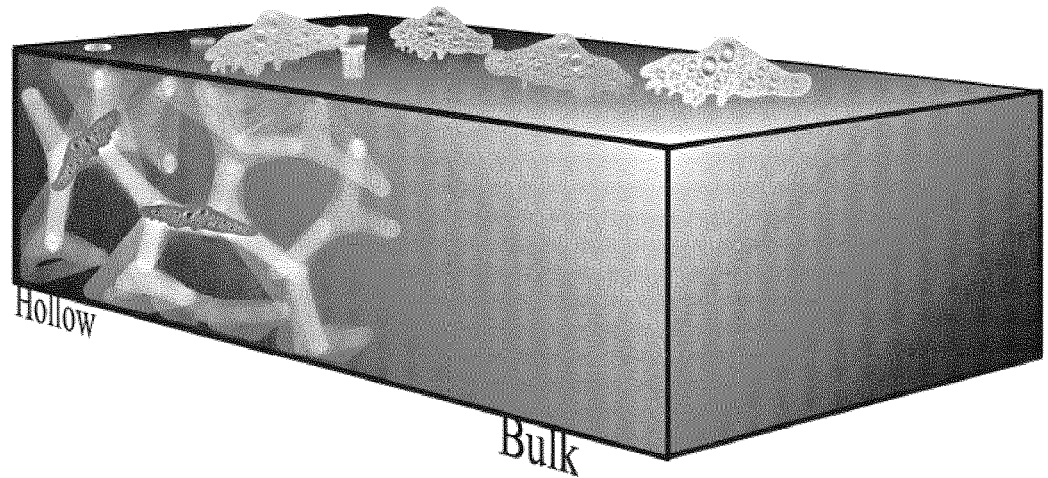
FIG. 8 is a schematic representation of *Acanthamoeba* cells entering into the porous polyacrylamide (dark with white tunnels) matrix in comparison to polyacrylamide bulk material (dark) where the cells stay on the surface.

A special distinguishing feature of a trap system according to the present invention is that it does not necessarily require an additional agent to attract the amoebae into the porous structure. The cells migrate into the tunnel-shaped pores naturally upon finding a way in on the outer surface of the substrate (schematically illustrated in FIG. 8).

Nevertheless, to further enhance the trapping effect, chemoattractant agents such as cAMP or others well known to those skilled in the art may still be incorporated into the hydrogel. Injecting such chemoattractant agents into the center of the hydrogel matrix will induce the migration of motile cells, e.g. of *Acanthamoeba*, towards the center of the hydrogel.

A trap system using a matrix according to the invention is particularly useful for sequestering and removing *A. castellanii* from a solution, such as liquid media, and especially from contact lens environments, thus preventing and/or reducing *A. castellanii* infections in contact lens users.

The present invention also provides a kit for cleaning contact lenses, comprising a solution for cleaning and/or storage of contact lenses and the matrix of the invention, e.g., in tablet form, wherein, preferably, the matrix is pre-packaged in an amount suitable for reducing or eliminating motile cells such as *A. castellanii* from one or two contact lenses in combination with the solution for cleaning or storing, preferably, storing contact lenses. The kit may also contain written instructions for said cleaning process.

Cleaning solutions for contact lenses may comprise hydrogen peroxide, but one-step cleaning solutions for hard or soft contact lenses on a different basis are also available. Alternative or additional components may be, e.g., polymer beads, surfactants/tensides and/or alcohol.

Often, cleaning solutions containing hydrogen peroxide need to be neutralized, e.g., by adding a further solution or a tablet. The matrix of the invention may be incorporated in such a neutralizing solution or tablet, or may be in a separate form.

The matrix of the invention is preferably incorporated into a storage solution for contact lenses. Alternatively or additionally, a container for storing contact lenses may also comprise the matrix of the invention.

The following examples are intended to illustrate the present invention but not to limit the scope thereof. All references cited in the application are fully incorporated herein.

Example 1: *Acanthamoeba* Culture

*Acanthamoeba* were cultured according to Gutekunst et al. (Beilstein J Nanotechnol. 2014, 5, 1393-1398). In brief, trophozoites of *Acanthamoeba castellanii* (*A. castellanii*, ATTC 30234) were cultured at room temperature in Peptone Yeast Glucose (PYG) 712 medium (20.0 g proteose peptone (BD, Sparks, USA), 1.00 g yeast extract (BD, Sparks, USA), 950 mL dist. $H_2O$, 10.0 mL 0.40 M $MgSO_4.7H_2O$ (AppliChem, Darmstadt, Germany), 8.00 mL 0.05 M $CaCl_2$ (AppliChem, Darmstadt, Germany), 34.0 mL 0.10 M sodium citrate.$2H_2O$ (Merck, Darmstadt, Germany), 10.0 mL 5.00 mM $Fe(NH_4)_2(SO_4)2.6H_2O$ (AppliChem, Darmstadt, Germany), 10.0 mL 0.25 M $Na_2HPO_4.7H_2O$ (Roth, Karlsruhe, Germany), 10.0 mL 0.25 M $KH_2PO_4$ (Roth, Karlsruhe, Germany), 50.0 mL 2.00 M glucose (Sigma-Aldrich Chemie GmbH, Steinheim, Germany)). In this axenic culture, the PYG 712 medium was regularly exchanged in the cell culture flasks in order to avoid encystment of *A. castellanii* trophozoites.

Example 2: Zinc Oxide Tetrapod Synthesis

The zinc oxide tetrapods (t-ZnO) were synthesized in a flame transport synthesis as shown by Adelung et al. (DE102010012385), Mishra et al. (Part Part Syst Char 2013, 30, 775-783; Kona 2014, 30, 92-110) and Mecklenburg et al. (Adv. Mater 2012, 24, 3486-3490). These tetrapod units with diameter dimensions ranging between 40 and 400 μm (arm diameters commonly used 500 nm-15 μm) were pressed into tablets with a density of 4-53 vol-% (commonly used 4-27 vol-%). After reheating (e.g., 1100° C.-1200° C., 5 h) the t-ZnO was interconnected and the tablets were used as a template for the polymerization of polyacrylamide.

Example 3: Template Mediated Polymerization of Polyacrylamide

Interconnected t-ZnO tablets were used as templates for polyacrylamide polymerization. A mixture of acrylamide solution (Bio-Rad, 40%, 1.00 mL), Bis solution (Bio-Rad, 2%, 10.0-250 µL), and ammonium persulfate solution (Sigma-Aldrich, 10%, aq., 30.0 µL) was filled up to a volume of 5.00 mL in a small beaker and degassed for 20 min in a desiccator. The solution was mixed with N,N,N',N'-tetramethylethyldiamine (TEMED, Bio-Rad, 10.0 µL) and the calculated volume for complete coverage of each t-ZnO tablet was poured on the tablet. After 1 h of polymerization the substrate was washed with bidest. $H_2O$.

Example 4: Hydrolysis of the ZnO Template Inside the Hydrogel

Figure 2:
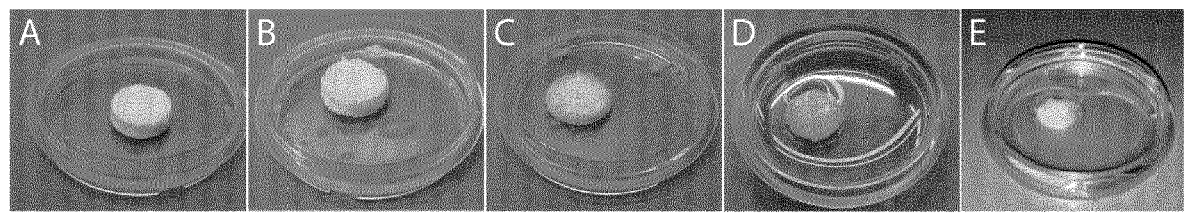
FIG. 2 shows the embedding and different stages of the zinc oxide tetrapod tablet hydrolysis in a polyacrylamide hydrogel. (A) t-ZnO sintered tablet (3 mm×11 mm); (B) acrylamide polymerization, (C) hydrochloride solution treatment for hydrolysis of the sacrificial t-ZnO tablet (1 M, 2 mL, t=3 min); (D) dissolving tablet and (t=11 min) (E) hydrolysis progression after 70 min.

The ZnO template was hydrolyzed with HCl (0.5-1.0 M, Sigma-Aldrich) for 24-120 h. After hydrolysis the hydrogel was washed with bidest. $H_2O$ until pH >6 was reached and complete swelling was achieved. Disinfection with 70% ethanol and washing under sterile conditions for 24 h with PYG 712 was performed before incubation with *A. castellanii*. The prepared substrates were used within 48 h. Hydrolyzing a t-ZnO tablet (typical dimensions: 1-3 mm×11 mm) embedded in polyacrylamide typically takes 2 to 4 days at pH 4. The production and hydrolysis of the matrix is shown in FIG. 2 at macroscopic and in FIG. 3 at microscopic scale.

Example 5: Effect of Swelling and HCl Treatment on the Mechanical Properties of the Polyacrylamide Matrix The stiffness of substrates is relevant to many applications, as it can control the adhesion and differentiation of cells. To test the effects of the swelling and of the HCl solution on polyacrylamide stiffness and integrity, different monomer to crosslinker ratios were used, as listed in Table 1, which lead to different Young's moduli.

TABLE 1

Acrylamide polymerization solutions.

|  | A [µL] | B [µL] | C [µL] |
| --- | --- | --- | --- |
| 40% Acrylamide | 1000 | 1250 | 1250 |
| 2% Bis | 200 | 500 | 1000 |
| HEPES buffer | 50.0 | 50.0 | 50.0 |
| Bidest. water | 3750 | 3200 | 2700 |
| 10% Ammonium persulfate | 30.0 | 30.0 | 30.0 |
| TEMED | 20.0 | 20.0 | 20.0 |

Figure 3:
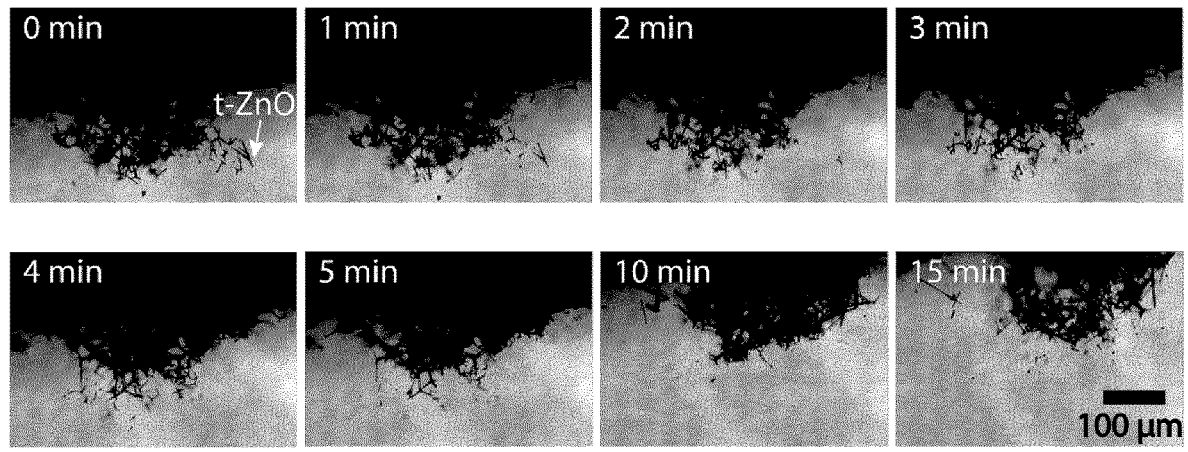
FIG. 3 depicts a time-lapse sequence of dissolving ZnO tetrapods (black) of a t-ZnO tablet embedded into polyacrylamide with hydrochloric acid (1.21 M, 2 mL) within 15 min (full dissolution occurs in 2 h). The arrow indicates a t-ZnO branch.

With microindentation experiments performed according to Gutekunst, et al. (Beilstein Journal of Nanotechnology 2014, 5, 1393-1398) it was determined that treatments even at pH values as low as 1 for 24 h did not significantly affect the mechanical properties of polyacrylamide, as shown in FIG. 3.

Example 6: Incubation of the Porous Hydrogel with Chemotaxis-Inducing Substances The polyacrylamide matrix, which had been hydrolyzed for 1-5 hours, was washed with Adenosine 3',5'-cyclic monophosphate solution (cAMP, Sigma-Aldrich, 0.01-10.0 mM) and then incubated for 3 to 4 days in cAMP solution. The solution was exchanged daily during this period.

Example 7: *Acanthamoeba castellanii* Cell Experiments

The sterile porous hydrogel samples were incubated with *A. castellanii* (ATTC 30234, 30.000 cells/mL) in a 6-well plate. After 0.5 to 2 hours, phase contrast microscope pictures (Olympus, IX-81/BX-43) were taken. Acanthamoebae migrated into the microporous hydrogel containing a chemotactic agent within 15 min up to a depth of 30-50 µm. The cells quickly moved through the tunnel-shaped pores, as shown in FIG. 7. A similar effect was observed in the absence of cAMP (FIG. 6). In general, the cells moved to dead ends, then turned around, and continued to move in an amoeboid manner through the tunnel-shaped pores until coming to larger cavities, where they remained for some hours.

The invention claimed is:

1. A porous hydrogel matrix comprising substantially interconnected tunnel-shaped micropores having a three-dimensional configuration corresponding to an interconnected hollow tetrapod network.

2. The matrix of claim 1, wherein the interconnected tunnel-shaped micropores have an average tunnel diameter from about 500 nm to about 15 µm.

3. The matrix of claim 1, wherein the tunnel-shaped micropores have an average tunnel length from about 20 µm to about 200 µm.

4. The matrix of claim 1, wherein the tunnel-shaped micropores have a ratio of tunnel length/tunnel diameter greater than 10.

5. The matrix of claim 1, wherein said matrix has a tunnel density between about 4 and about 53 volume percent.

6. The matrix of claim 1, wherein the hydrogel matrix comprises a material selected from the group consisting of polyacrylamide, polyethylene glycol, poly(N-isopropylacrylamide), poly(2-hydroxyethyl methacrylate), poly(acrylic acid) and copolymers thereof.

7. The matrix of claim 1, wherein said matrix comprises cyclic adenosine monophosphate.

8. The matrix of claim 1, wherein said matrix is produced by a method comprising
    a) providing a solution of a hydrogel-forming material;
    b) providing a template material with a three-dimensional configuration corresponding to the negative configuration of a desired interconnected porous structure of the hydrogel matrix, said template material comprising interconnected zinc oxide tetrapod networks;
    c) casting the solution of hydrogel-forming material onto the template material to form the hydrogel matrix; and
    d) removing the template material from the hydrogel matrix by acid hydrolysis of the template material.

9. The matrix of claim 1, wherein said matrix comprises a template material with a three-dimensional configuration corresponding to the negative configuration of the interconnected porous structure of the hydrogel matrix, said template material comprising interconnected zinc oxide tetrapod networks.

10. A method of reducing or eliminating motile cells from a solution or from an object in contact with a solution, comprising contacting said solution with the matrix of claim 1.

11. The method of claim 10, wherein the motile cells are *Acanthamoeba castellanii*.

12. The method of claim 10, wherein the solution is selected from the group consisting of water, contact lens cleaning solution, contact lens storage solution and cell culture medium.

13. A kit for cleaning contact lenses, comprising a solution for cleaning contact lenses and/or a solution for storing contact lenses, and the matrix of claim 1.

14. A method for forming the porous hydrogel matrix of claim 1, said method comprising:

a) providing a solution of a hydrogel-forming material;
b) providing a template material with a three-dimensional configuration corresponding to the negative configuration of a desired interconnected porous structure of the hydrogel matrix, said template material comprising interconnected zinc oxide tetrapod networks;
c) casting the solution of hydrogel-forming material onto the template material to form the hydrogel matrix; and
d) removing the template material from the hydrogel matrix by acid hydrolysis of the template material.

15. The matrix of claim 1, wherein a majority of junctions formed by the micropores form a tetrahedron angle.

* * * * *